United States Patent
Rutten et al.

(10) Patent No.: US 6,278,897 B1
(45) Date of Patent: Aug. 21, 2001

(54) MEDICAL ELECTRICAL LEAD AND INTRODUCER SYSTEM

(75) Inventors: Jean J. G. Rutten, El Bocholtz; Karel Smits, Ja Munstergeleen; Nicolaas Lokhoff, He Kerkrade; Paulus Van Venrooij, Ez Hoensbroek, all of (NL)

(73) Assignee: Medtronic, INC, Minneapolis, MN (US)

( * ) Notice: Subject to any disclaimer, the term of this patent is extended or adjusted under 35 U.S.C. 154(b) by 0 days.

(21) Appl. No.: 09/204,314

(22) Filed: Dec. 3, 1998

(51) Int. Cl.$^7$ ....................................... A61N 1/05
(52) U.S. Cl. ........................................... 607/122; 607/123
(58) Field of Search .................... 607/122, 123, 607/130, 131, 126

(56) References Cited

U.S. PATENT DOCUMENTS 4,057,067 * 11/1977 Lajos .

(List continued on next page.)

OTHER PUBLICATIONS

U.S. application No. 08/794,402, Kruse et al., filed Feb. 1997.

*Primary Examiner*—Carl H. Layno
(74) *Attorney, Agent, or Firm*—Thomas F. Woods; Michael J. Jaro; Harold Pattom

(57) ABSTRACT

A medical electrical lead and introducer system. The lead is a single pass, dual chamber lead, which features in one embodiment an atrial tine. The introducer system is particularly designed for introduction of single pass, dual chamber lead which has an atrial tine. The introducer system facilitates the introduction of a such lead into a patient's heart while safeguarding the tine from damage due to kinking during lead positioning. The lead is a single pass lead which features an atrial tine while the introducer system is particularly designed for introduction of a such lead into a patient's heart so as to safeguard the tine from damage due to kinking during lead positioning. The lead is designed so as to electrically couple both the atrium and the ventricular chambers of the heart. The lead generally features several lengths each having differing stiffness as well as a preformed bend. The lead also features a atrial tine having an electrode at the tip. Due to the relatively fragile as well as difficult to maneuver lead, an introducer system is also disclosed. The introducer system is particularly designed to introduce such a lead. In use a removable tubing split element surrounds the atrial tine area of the lead while it is disposed through the introducer sheath, the split element both blocks the tine from lateral movement and fills up the space between the lead body and the introducer, thereby preventing blood leakage through the introducer. The element also has a longitudinal split for receiving the atrial tine while holding it against transverse movement when the lead is being repositioned. After optimal positioning of the lead, the tubing split element is withdrawn, and then the introducer is withdrawn. The tubing split element is a generally cylindrical piece of TEFLON, here called a tube split element, or just a "tube split", is positioned around the lead body in the atrial tine area. The tube split element has a thickness which substantially fills the radial gap between the smaller diameter lead body and the introducer inner cylindrical wall, and has a longitudinal separation, or split, which accommodates the atrial tine, thereby permitting the tine to extend longitudinally but not transversely. The tubing split element is preferably mounted on the lead at the time of lead assembly. It has a length sufficient to extend proximally out of the introducer so that it can be withdrawn, and has a longitudinal tear line whereby the element can be separated and removed from the lead after final positioning of the lead.

43 Claims, 9 Drawing Sheets

U.S. PATENT DOCUMENTS

| | | |
|---|---|---|
| 4,553,961 | 11/1985 | Pohndorf et al. . |
| 4,585,013 | 4/1986 | Harris . |
| 5,129,405 | 7/1992 | Milijasevic et al. . |
| 5,312,360 | 5/1994 | Behl . |
| 5,443,492 * | 8/1995 | Stokes et al. .......................... 607/131 |
| 5,628,779 * | 5/1997 | Bornzin et al. . |
| 6,024,764 * | 2/2000 | Schroeppel . |
| 6,055,457 * | 4/2000 | Bonner ................................. 607/126 |

* cited by examiner

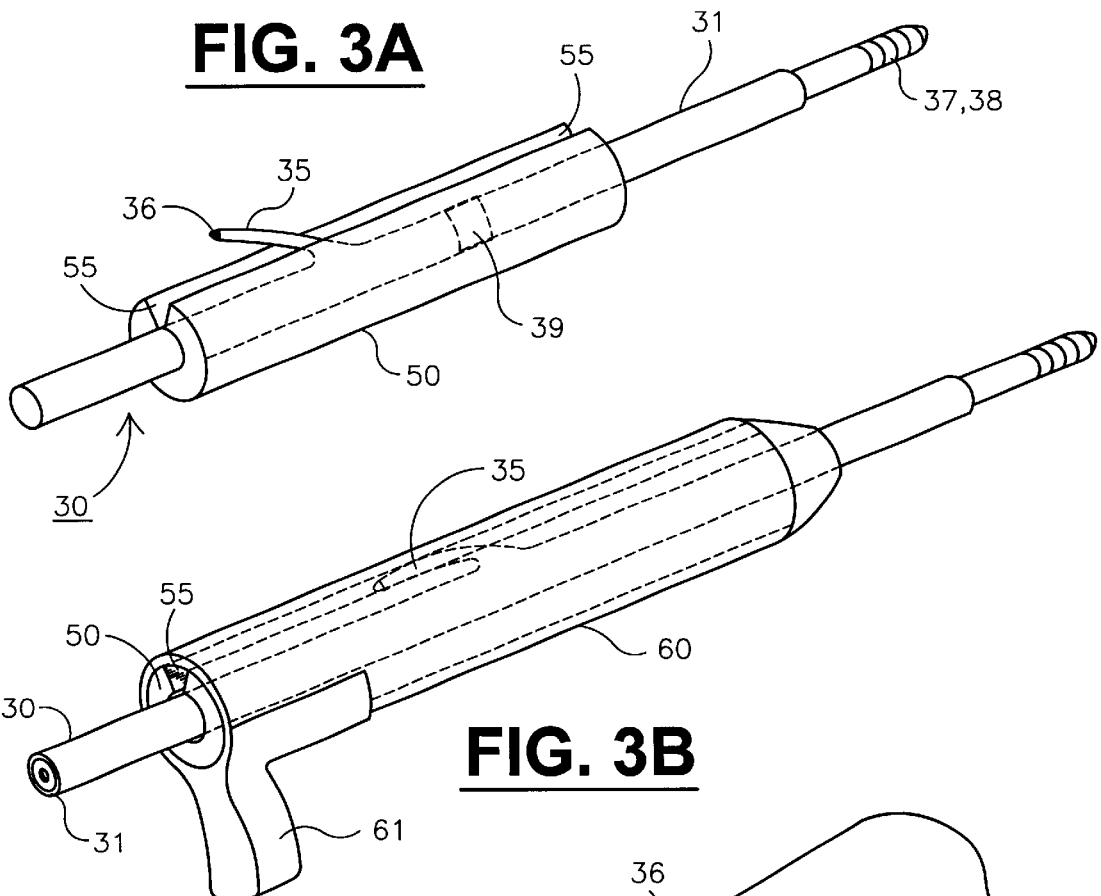
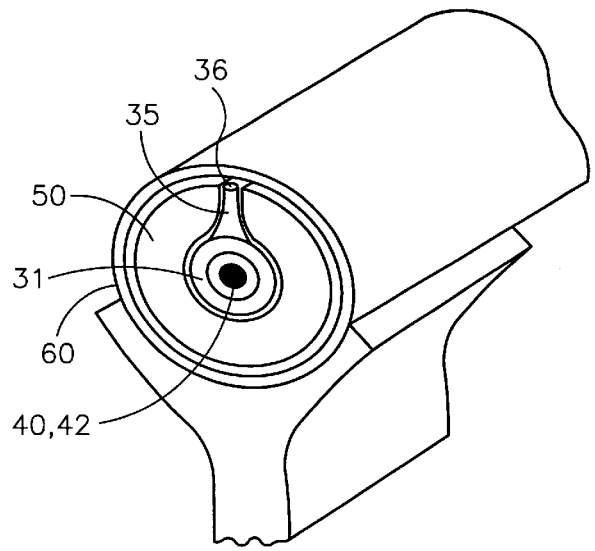

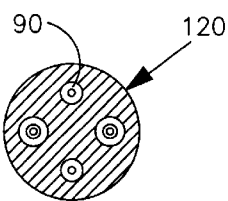
SECTION 5A-5A
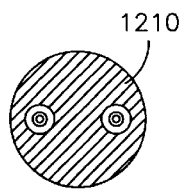
SECTION 5B-5B
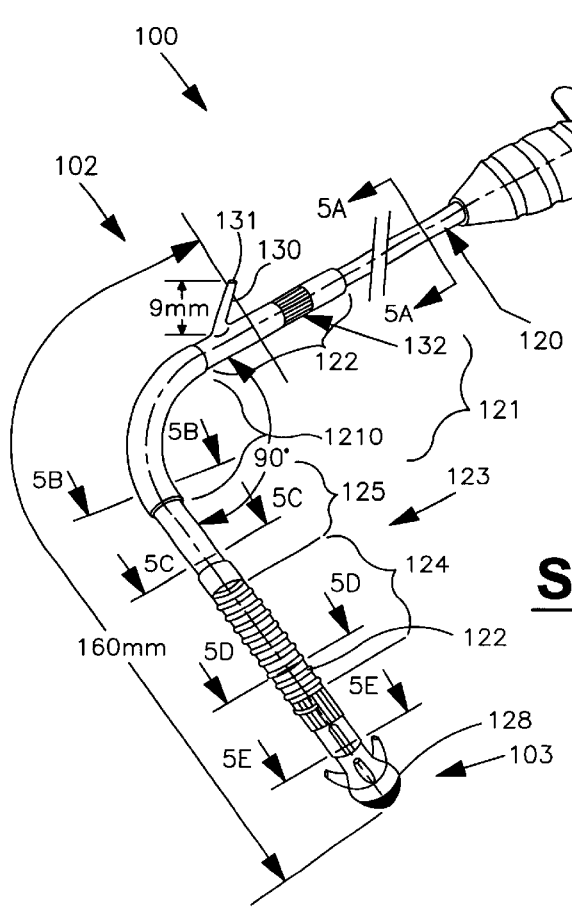
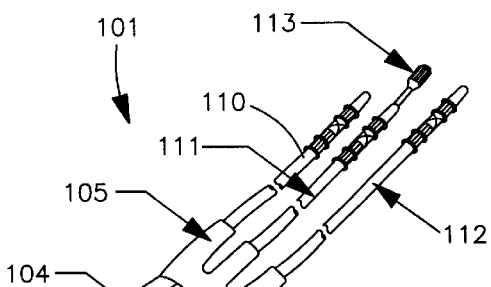
SECTION 5C-5C
SECTION 5E-5E
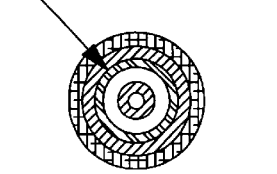
FIG. 5
SECTION 5D-5D

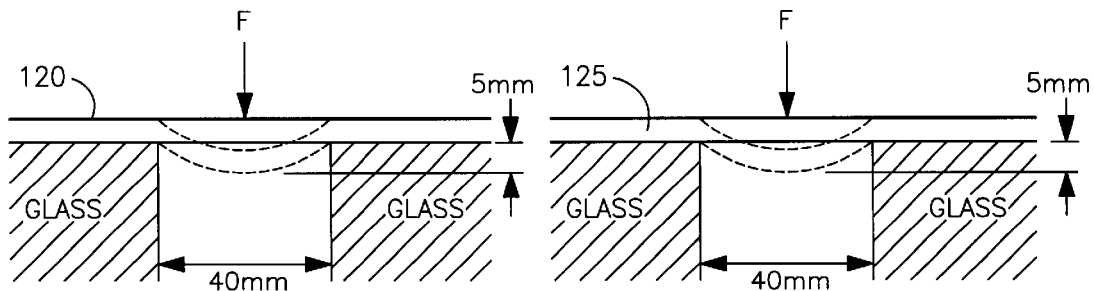
FIG. 6B
FIG. 6E
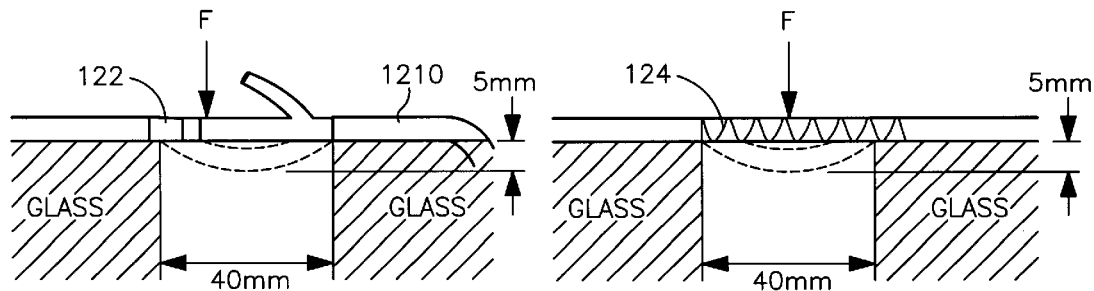
FIG. 6C
FIG. 6F
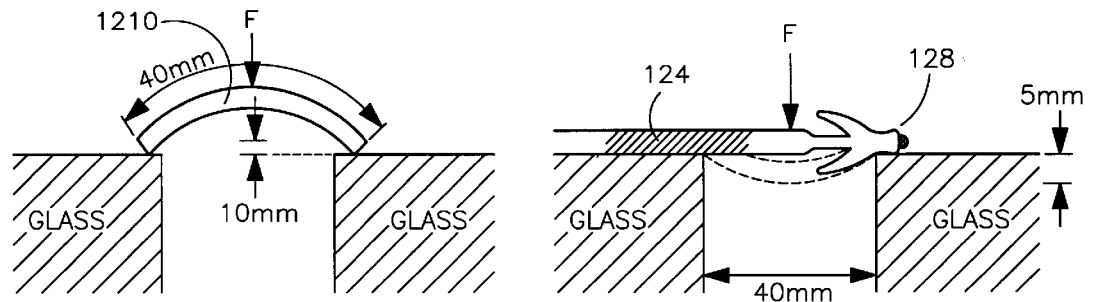
FIG. 6D
FIG. 6G

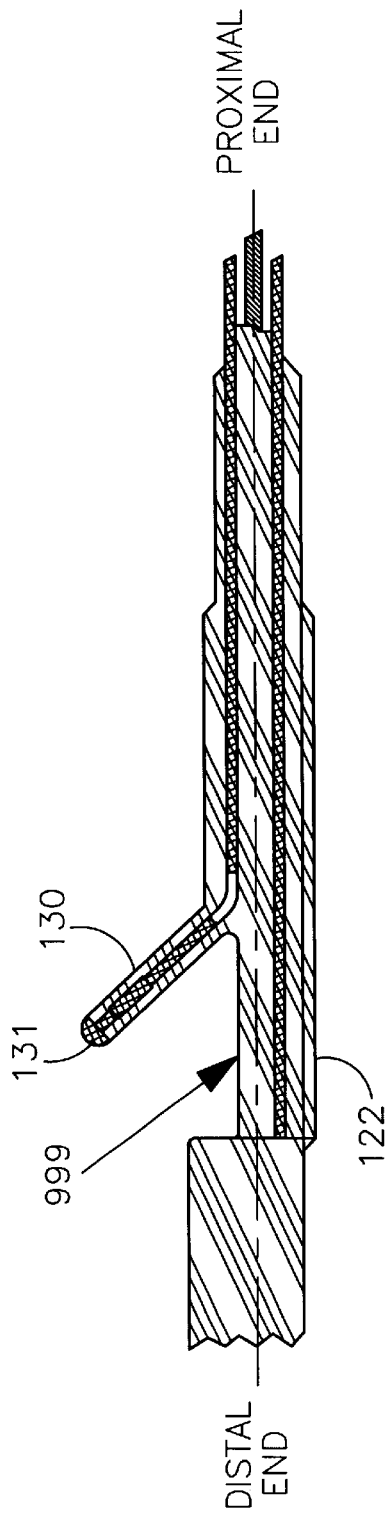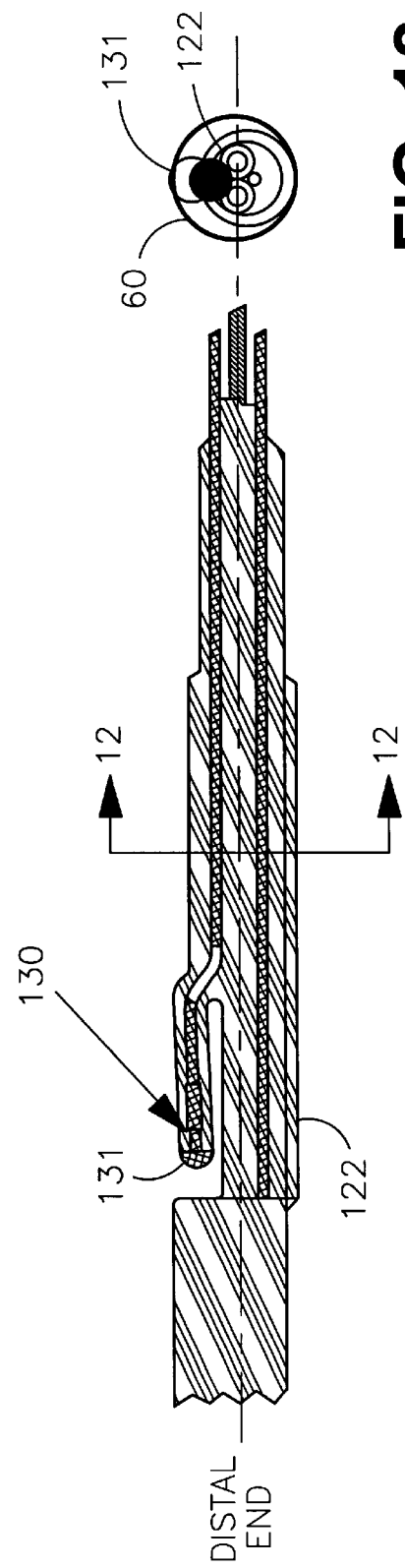

MEDICAL ELECTRICAL LEAD AND INTRODUCER SYSTEM

FIELD OF THE INVENTION

This invention lies in the area of medical electrical stimulation, and, more particularly, a medical electrical lead and introducer system.

BACKGROUND OF THE INVENTION

In many cardiac pacing, defibrillation and cardioversion applications, it has been found useful to employ an atrial "tine" on the lead, to improve positioning and fixation of the lead electrode against or in close proximity to the atrial wall. For a DDD type pacing lead, for example, where a single lead is used to pace and sense in the ventricle and the atrium, there is no distal end of the lead within the atrium which can be simply guided into a position where it can efficiently pace and sense. Rather, it is necessary to include some design feature to ensure that the lead portion carrying the atrial electrode or electrodes is held close enough to the atrial wall to provide reliable operation. It has been found that incorporation of an atrial tine, which in this context is a relatively small arm, or extension from the main lead body, can provide a marked improvement in terms of holding the atrial electrode or electrodes in good position. Examples of leads which use such atrial tines are shown in the patent art, e.g., U.S. application, Kruse et al., Ser. No. 08/794,402, filed Feb. 3, 1997. It is to be understood that the atrial tine carries one or more electrodes at its distal end, and a coil conductor or conductors for electrically connecting to such electrode(s).

Conventionally, the lead is inserted into the heart through an introducer, which is a hollow tube having in inner lumen of greater diameter than the lead body diameter. The introducer is first inserted into a vein and then down into the heart, in a well known manner. Following this, the lead is guided through the introducer into the heart, and positioned for optimum pacing and sensing. Generally, re-positioning is required, as often the first attempt does not produce the best possible position for stimulation threshold. The re-positioning involves withdrawing the lead back through the introducer, and then reinserting it, e.g., so that the far distal end is positioned in the right ventricular apex. A problem arises in such re-positioning, where the lead carries an atrial tine. When the lead is withdrawn, the atrial tine is often caused to kink within the introducer. Extending the tine longitudinally is not a problem, but transverse kinking often occurs, which produces high stresses in the electrode coil (conductor). Such kinking can be caused several times, depending on how many times the physician needs to re-position the lead. Tests have shown that this can lead to coil breakage, which would destroy the atrial function of the lead. Coil breakage in a lead is, of course, disastrous for the patient, and any condition which could accelerate such a result must be avoided.

Another problem that bothers many physicians during lead introduction is that of blood leakage through the introducer. The introducer inner diameter is necessarily larger than the lead body diameter, in order to permit easy passage through the introducer, and to accommodate, e.g., fixation type tines as may be positioned at the distal end of the lead, and which extend laterally from the lead body. For example, for a 14 French introducer and an 8 French body diameter lead, a lot of blood leakage occurs between the lead body and the introducer while the physician maneuvers the lead through the introducer and into position.

It is to be noted that generally it is not a solution to withdraw the introducer before repositioning the lead. If this is done, it is necessary to squeeze the vein around the lead body in order to reduce blood leakage. Such a procedure becomes even more difficult, if not impossible for one physician, when a stylet has to be inserted for the repositioning. In any event, if the repositioning takes a long time, there is such significant blood leakage that this is unacceptable to most physicians. Further, if the introducer is not in place during repositioning, the atrial tine may enter a vein junction or other unintended area, and thus the introducer is kept in place to protect against such a possibility.

In view of the above, it is seen that there exist several problems with the current method and apparatus for introducing leads into a patient's heart for cardiac treatment. It is desirable to provide an improvement to reliably safeguard against atrial tine transverse kinking, and also to reduce the blood leakage through the introducer at time of lead implantation. It is an object of this invention to provide a simple but effective way to both prevent transverse tine kinking and to substantially eliminate the undesirable blood leakage through the introducer.

SUMMARY OF THE INVENTION

A medical electrical lead and introducer system. The lead is a single pass, dual chamber lead, which features in one embodiment an atrial tine. The introducer system is particularly designed for introduction of single pass, dual chamber lead which has an atrial tine. The introducer system facilitates the introduction of a such lead into a patient's heart while safeguarding the tine from damage due to kinking during lead positioning. The lead generally features several lengths each having differing stiffness as well as a preformed bend. The lead also features a atrial tine having an electrode at the tip. Due to the relatively fragile as well as difficult to maneuver lead, an introducer system is also disclosed. The introducer system feature a removable tubing split element surrounds the atrial tine area of the lead while it is disposed through the introducer sheath, the split element both blocks the tine from lateral movement and fills up the space between the lead body and the introducer, thereby preventing blood leakage through the introducer. The element also has a longitudinal split for receiving the atrial tine while holding it against transverse movement when the lead is being repositioned. After optimal positioning of the lead, the tubing split element is withdrawn, and then the introducer is withdrawn. The tubing split element is a generally cylindrical piece of TEFLON, here called a tube split element, or just a "tube split", is positioned around the lead body in the atrial tine area. The tube split element has a thickness which substantially fills the radial gap between the smaller diameter lead body and the introducer inner cylindrical wall, and has a longitudinal separation, or split, which accommodates the atrial tine, thereby permitting the tine to extend longitudinally but not transversely. The tubing split element is preferably mounted on the lead at the time of lead assembly. It has a length sufficient to extend proximally out of the introducer so that it can be withdrawn, and has a longitudinal tear line whereby the element can be separated and removed from the lead after final positioning of the lead.

In practice, the physician first inserts the introducer so that it extends into the patient's heart. Then, the lead, with the tubing split element in place around it, is passed through the introducer and into the heart. For a DDD type lead, the distal end is positioned in the right ventricular apex. It is then withdrawn and re-positioned as many times as necessary, to find the best location for optimum threshold. During these re-portioning steps, the tubing element prevents transverse kinking of the atrial tine, or tines, and minimizes blood leakage through the introducer. After this, the physician first withdraws the tubing split element proximally to clear the end of the introducer, separates it and removes it from the lead. Then the introducer is withdrawn and likewise removed from the lead. After this, of course, the proximal end of the lead is attached to the stimulus device, e.g., pacemaker, defibrillator, etc.

BRIEF DESCRIPTION OF THE DRAWINGS

FIG. 3A is a diagrammatic representation of a tubing split placed on a lead, in accord with this invention; FIG. 3B is a diagrammatic representation of the lead with tubing split element as placed within an introducer; and FIG. 3C is a cross-sectional view through the assembly of FIG. 3B

FIG. 5 depicts the lead used with the present invention.

FIGS. 6B–6G depict the testing rigs used for the measurements illustrated in FIG. 6A.

FIG. 10 depicts an alternative embodiment of lead and, in particular, a detailed view of a lead having an improved tine.

FIG. 11 depicts the tine folded forward for introduction and particularly shows the tine nestling into cavity 999.

FIG. 12 is a section view depicting the folded tine within an introducer sheath.

The FIGS. are not necessarily to scale.

DESCRIPTION OF THE PREFERRED EMBODIMENTS

It is to be understood, that the present invention concerns either a medical electrical lead or an introducer system to introduce such a medical electrical lead or both. The introducer disclosed, however, is not limited to use only in introducing atrial or ventricular pacing leads, and may be employed in introducing many of various types of therapeutic or diagnostic devices including transvenous leads intended to be disposed at various places within patient 10, including, for example, leads intended to be disposed within the patient's coronary sinus, as well as various other types of electrical leads, including nerve, muscle or defibrillation leads. It is to be further understood, moreover, that the present invention may be employed in introducing many of various types of therapeutic or diagnostic catheters and is not limited only to the introduction of electrical leads. For purposes of illustration only, however, the present invention is below described in the context of the introduction of endocardial leads. Moreover, the lead disclosed should not be read as only being limited to endocardial leads; rather the term "lead" is used in its broadest sense, and is intended to include any type of usable medical catheter, include those for administering either fluids or electrical stimulation or both. For purposes of illustration only, however, the present invention is below described in the context of an endocardial lead. Thus, below is illustrated a medical electrical lead and introducer system. The lead is a single pass, dual chamber lead, which features in one embodiment an atrial tine. The introducer system is particularly designed for introduction of single pass, dual chamber lead which has an atrial tine. The introducer system facilitates the introduction of a such lead into a patient's heart while safeguarding the tine from damage due to kinking during lead positioning.

Figure 1A:
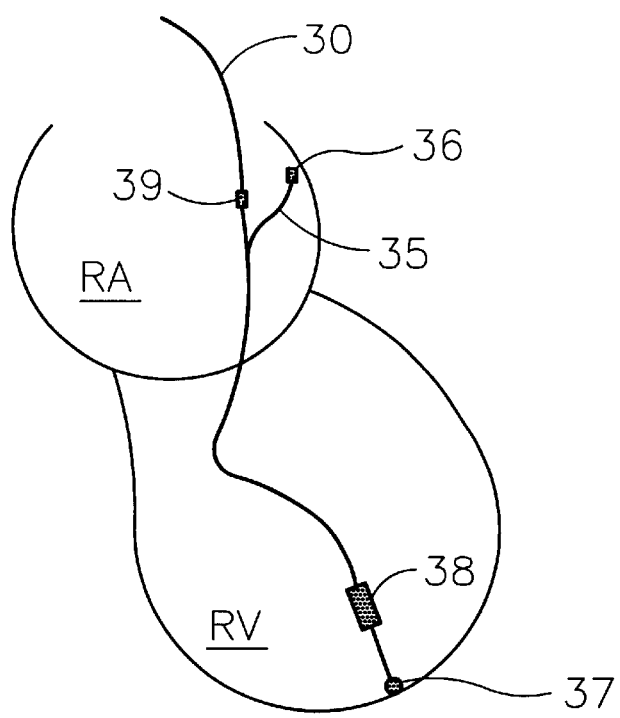
FIG. 1A is a diagram showing a DDD type lead with an atrial tine, positioned in a patient's heart.

Referring now to FIG. 1A, there is shown a DDD type (also known as a "single pass, dual chamber") lead positioned within a patient's heart. The lead 30 is shown with the distal end in the right ventricular apex, and having an electrode 37 fixed against the inside of the heart. Another electrode, or electrodes 38 may also be employed. It is to be understood that the invention is not limited to leads for just pacing, and indeed in a preferred embodiment the lead is used with a pacemaker-cardioverter-defibrillator system. However, for exemplary purposes only, the lead is illustrated as a DDD single pass lead for pacing and sensing in the ventricle and in the atrium. The lead has at least one atrial tine, shown at 35, which is placed along the length of the lead such that when the distal end is properly fixed at the ventricular apex, the tine 35 can be positioned against the atrial wall for efficient pacing and sensing through electrode 36. For a bipolar arrangement, a ring electrode as shown at 39 can be used.

Figure 1B:
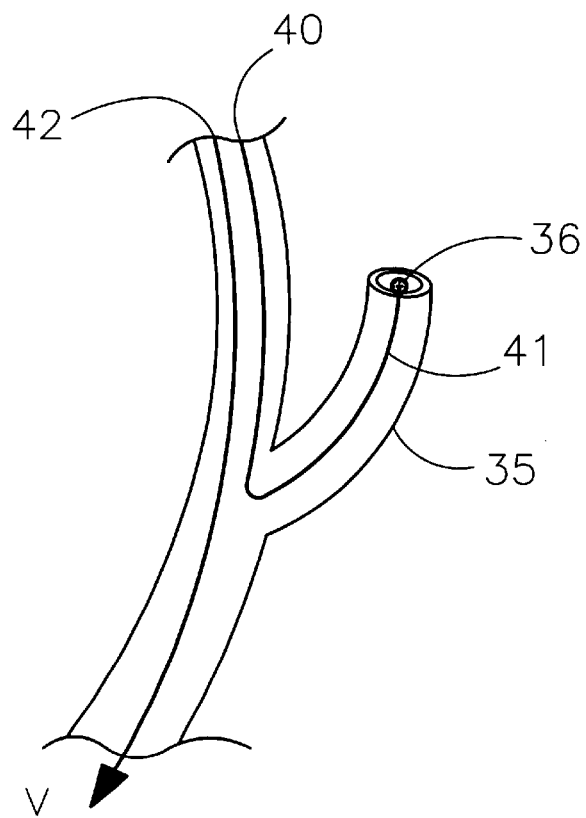
FIG. 1B is an enlarged representation of the atrial portion of such a DDD type lead, illustrating the atrial tine.

Referring to FIG. 1B, there is shown an enlarged diagram of the atrial portion of the lead, illustrating tine 35. Electrode 36 is electrically connected to the proximal end of the lead through conductor 42 and tine conductor 41. The problem of conductor stress due to transverse kinking affects the lead in this area, i.e., where the conductor 41 extends into the atrial tine, such that it is vulnerable to lateral or transverse bending. Although not shown in this figure, a separate conductor is provided for ring electrode 39. As is shown, a conductor (or conductors) 42 extends through the lead to the ventricular electrode (or electrodes).

Figure 2:
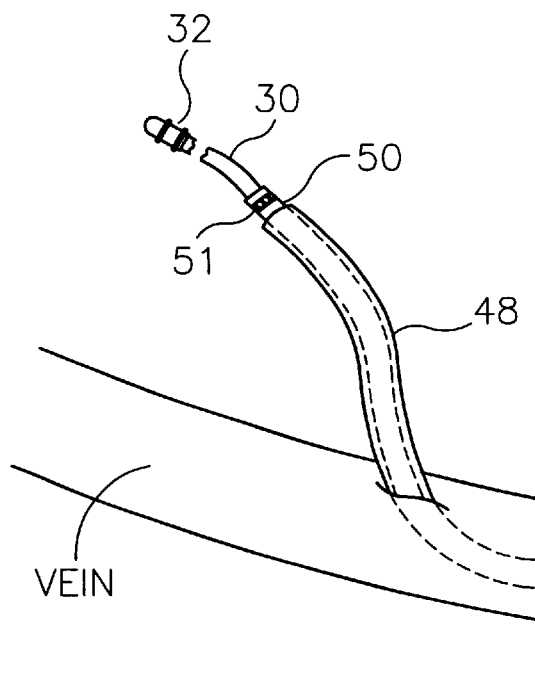
FIG. 2 is a diagram illustrating an introducer extended into a patient's vein, and the combination lead and tubing split element of this invention inserted into the introducer.

Referring now to FIG. 2, there is shown a diagram of an introducer 48 positioned into a vein or other vessel. A lead assembly, being the combination of lead 30 and tubing split element 50, has been inserted into and through the introducer. Lead 30 has a proximal end 32, for connecting to a pacemaker or other stimulator device. As here illustrated, the proximal end of tubing split element 50 (shown in greater detail in FIG. 3A) extends out of the introducer, so that the physician is enabled to grip it and withdraw it over the lead. Also illustrated is a grip portion 51, which may be of a higher friction material, to facilitate withdrawal. In practice, the lead and tubing split assembly is first inserted into the introducer, and pushed until the distal end of the lead 30 is at the ventricular apex. The physician attempts to make good contact with the endocardium, and checks this in a well know manner. As indicated above, it rarely happens that the first attempt is successful in finding the optimum location, and accordingly in a normal procedure the lead is withdrawn backwards through the introducer and then repositioned, usually several times. Distal tines 44 are illustrated as a conventional fixation means for holding the lead distal tip in the finally selected position.

The tubing split element, as disclosed in further detail with reference to FIGS. 3A, B and C, is suitably made as one integral piece of TEFLON, or similar low-friction material. The element preferably has a length in the range of about 8–15 cm, and more specifically around 10–12 cm. The inner diameter of the tubing split element is about the same or just smaller than the lead on which it is mounted, so as to clamp the lead around the atrial tine. The outer diameter is just less than the inner diameter of the introducer. It is to be understood that the length of the tubing split element will depend upon the lead design, including such factors as the length of the lead, pre-shape sections, etc.

Referring now to FIGS. 3A, 3B and 3C, there are shown detailed diagrammatic representations of the lead assembly in accordance with this invention. FIG. 3A shows the tubing split element 50 in combination with a portion of the atrial tined lead 30. As indicated, the atrial tined lead has distal electrodes 37, 38 for positioning in the ventricle; and atrial ring electrode 39 for positioning in the atrium. The lead has a tubular casing, or body 31, and also has an atrial tine 35, with an atrial tip electrode 36. Tine 35 is shown extended out of split 55, which in this embodiment runs the full length of tubing split element 50. As is seen, split 55 provides for radial extension of tine 35 away from the axis of lead 30, but inhibits lateral, or transverse bending of the tine. FIGS. 3B and 3C show the lead assembly 30, 50 inserted into a standard introducer 60, illustrated as having a handle 61. In this arrangement, the tine 35 is constrained both by the walls of the split 55 and by the inner wall of introducer 60. It is seen that the tine can be flexed longitudinally, but in the event of longitudinal movement of the lead assembly relative to the introducer, tine 35 cannot be subjected to transverse movement with resulting kinking. Although not illustrated in FIG. 3B, tubing split element 50 is preferably long enough to extend a short distance proximally from the proximal end of the introducer, as illustrated in FIG. 2, to facilitate withdrawal. As seen in the cross-sectional view of FIG. 3C, tubing split element 50 virtually fills up the space between lead 30 and the wall of introducer 60, thereby reducing blood leakage. Lead 30 is illustrated with conductors 40, 42 positioned at the axis of the lead. Of course, the lead may have more than two conductors running within the tube casing, or body 31.

Figure 4:
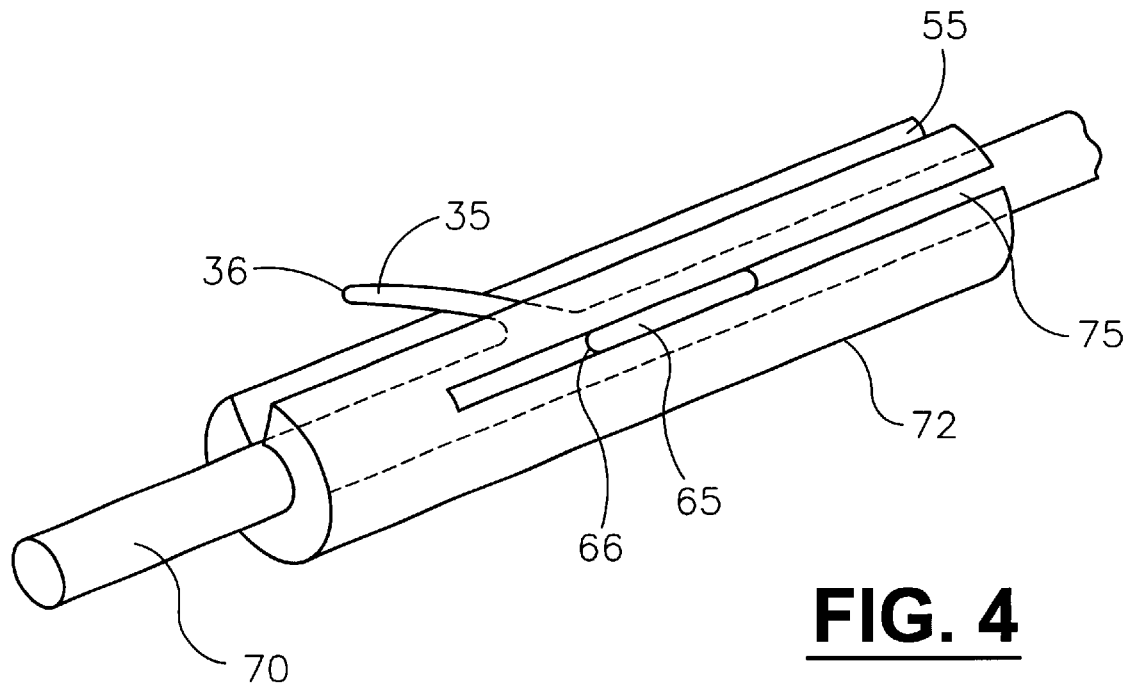
FIG. 4 is a diagrammatic representation of a tubing split for accommodating two atrial tines.

Referring now to FIG. 4, there is shown a diagrammatic representation of a lead assembly in accordance with this invention, wherein the lead 70 has two atrial tines, indicated at 35 and 65. The atrial tines have respective tip electrodes 36 and 66. In this embodiment, the tubing split element 72 has a first split 55, which may extend the full longitudinal length of element 72; and a second split 75 which extends less than the full length of the element, to enable a single piece element which can be mounted onto the lead and withdrawn in the same manner as the single split embodiment. In this manner, the tubing split element can be designed to accommodate plural atrial leads.

FIG. 5 depicts the lead used with the present invention. As seen, lead 100 has a proximal end 101, a middle 102 and a distal end 103. Proximal end features a trifurcation 104 and strain relief 105. These components support the conductors as they exit the proximal end of the lead body and join into connectors 110, 111 and 112 as seen. Connectors 110 and 111 are compatible with standard IS-1 and 112 is compatible with standard DF-1. Conductors are hollow coiled conductors such that a stylet 113 may be introduced therein to facilitate lead positioning. Conductors are preferably closely spaced coils of MP35N, for use in lower voltage pacing devices, while the higher voltage defibrillation conductor coils are fashioned from MP35N/AG as well known in the art. Also located near proximal end of lead is anchoring sleeve 114 as is also well known in the art, as used in the Medtronic Model 5032 lead.

Middle 102 of lead generally refers to the entire length of the lead, running from between the proximal end's trifurcation 104 and strain relief 105 to the distal end's tip electrode. Middle 102 of lead has three sections having different degrees of flexibility or stiffness. Proximal portion 120 of middle 102 is preferably less stiff than distal portion 123 of middle 102 while central portion 121 of middle 102 is more stiff than distal portion 123 or proximal portion 120. Distal portion 123, moreover has additional stiffness differences within itself, as disclosed more fully below.

As seen, central portion 121 features a tine 130 having a tine electrode 131 at the tip. Central portion further features a ring electrode 132. Tine electrode and ring electrode are of standard construction, tine electrode having a surface area of 4 sq. mm. and made of a porous electrode material such as sintered spherical platinum powder, as is well known in the art. Tine is preferably 9 mm in length, although other lengths between 1 to 20 mm may also be used. Ring electrode has a surface area of 33 sq. mm. and is fashioned from a platinum iridium alloy as well known in the art. Central portion is generally the same as that found in the prior Medtronic leads model 5032 and model 5038. Further details of the construction of central portion may be seen in the patent application "Single Pass Medical Electrical Lead" of Kruse et al., incorporated herewith by reference (pending U.S. patent application Ser. No. 08/794,402).

Distal portion 123 has essentially two separate sections. Stiffest distal section 124 is located distal to the less stiff distal section 125. In the preferred embodiment the additional stiffness to stiffest distal section is provided by a defibrillation electrode, seen here as 127. It should be understood, however, that the lead may still be made to have the proper stiffness without resorting to a defibrillation coil. For example, if only a single pass pacing lead is desired (i.e. without the need for a defibrillation coil) then distal section may still be made to be stiffer through other means than a unnecessary electrode coil. Such other means may include metal or polymeric stiffening elements, as well as geometric enhancements to the lead body (e.g. variance of the cross sectional shape.) The particularly elements used to provide the handling characteristics to the lead body are not essential, so long as a lead results which provides acceptable atrial and ventricular electrical coupling. Positioned at the distal end of lead is a pacing electrode assembly 128 having corresponding tines, as is well known in the art. In the preferred embodiment, this distal pacing electrode assembly 128 is provided by the pacing electrode from the prior art Medtronic Model 5032.

An important feature of this lead is the different degrees of stiffness or flexibility as well as the 90° pre-shape to central portion. Of course the pre-shape may be made in any angle within the range of 45 to 135 degrees. Ninety degrees is merely the preferred bend. As already described above, middle 102 has three portions each having differing degrees of stiffness: Proximal portion 120 of middle 102 is less stiff than distal portion 123 of middle 102; central portion 121 of middle 102 is more stiff than either proximal portion 120 or distal portion 123. In addition, distal portion 123 itself has two differing areas of stiffness: Stiffer distal section 124 is located proximal to the less stiff proximal section 125. Thus the various sections along the lead body may be characterized in descending order of relative stiffness as follows: central portion 121, distal section 124 of distal portion 123, proximal section 125 of distal portion 123, and finally proximal portion 120.

At implantation it is believed that the stiffer distal portion tends to provide support to the middle and particularly to the tine electrode 131 such that cardiac motion tends to force the electrode against the atrial wall. Moreover, the overall length of the lead between the atrial electrode and the distal tip is preferably longer than conventionally indicated in the particular patient. That is, standard single pass leads have a distance between the atrial electrode and the distal end roughly corresponding tot he actual distance between the atrial wall and the ventricular apex. In the preferred embodiment the present invention is sized such the atrial electrode distal tip distance is greater than that indicated by the patients anatomy. Through the use of a elongated lead, the additional lead body cooperates with the apex such that the atrial electrode is forced against the atrial wall.

Although the lead used in the present invention provides important, novel and superior performance as compared to prior single pass lead designs, it may nonetheless be assembled from components of prior leads. Tip electrode assembly 128 and corresponding ring is the same as used in the Medtronic Lead Model 6932. defibrillation coil 124 is the same as used in the Medtronic Lead Model 6933 or 6937. Distal section 125 is the same as used in the Medtronic Lead Model 5032. Central portion 121 is the same as used in the Medtronic Lead Model 14107, further details h may be found in the above-mentioned Kruse patent application. Central portion 121 including tine 130, tine electrode 131 and ring electrode 132 as well as proximal portion 120 is the same as used in the Medtronic Lead Model 5032.

Figure 6A:
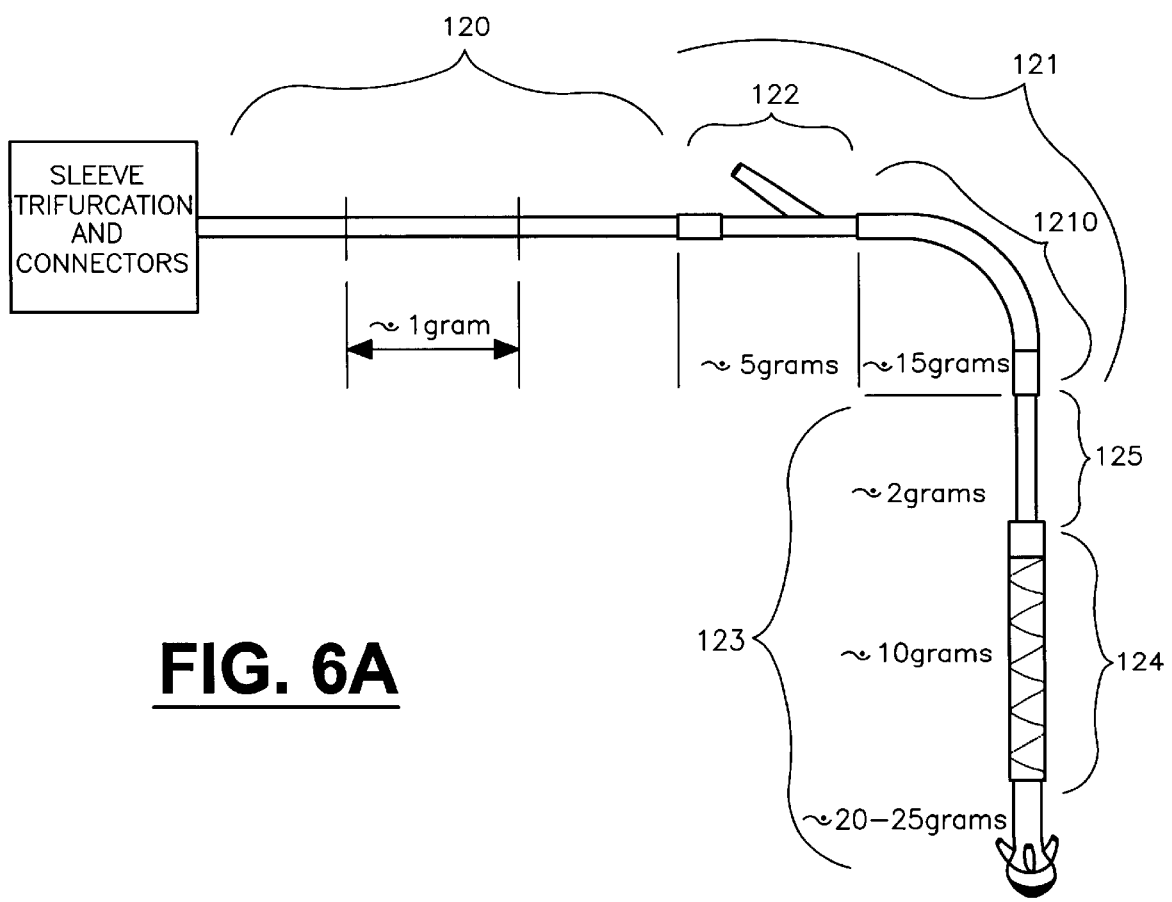
FIG. 6A illustrates the relative stiffness along the relevant portions of the lead body.

FIG. 6A illustrates the various stiffnesses along the relevant portions of the lead body. As seen proximal portion 120 of middle 102 (which, as described above, generally refers to the entire length of the lead, running from between the proximal end's trifurcation 104 and strain relief 105 to the distal end's tip electrode) has a bending stiffness of approx. 1 gram (as measured by the testing rig and procedure shown in FIG. 6B.)

Central portion 121 has two sections; proximal section 122 of central portion 121 has a bending stiffness of approx. 5 grams (as measured by the testing rig and procedure shown in FIG. 6C) and distal section 1210 of central portion 121 has a bending stiffness of approx. 15 grams (as measured by the testing rig and procedure shown in FIG. 6D.)

Distal portion 123 has two sections; proximal section 125 of distal portion 123 has a bending stiffness of approx. 2 grams (as measured by the testing rig and procedure shown in FIG. 6E) and distal section 124 of distal portion 123 has a bending stiffness of approx. 10 grams (as measured by the testing rig and procedure shown in FIG. 6F.)

Finally distal tip electrode 128 has a bending stiffness of approx. 20 grams (as measured by the testing rig and procedure shown in FIG. 6G).

FIGS. 6B–6G depict the testing rigs used for the measurements illustrated in FIG. 6A. Proximal portion 120 of middle 102 had its bending stiffness measured by the testing rig and procedure shown in FIG. 6B. As seen 40 mm length of proximal portion 120 of lead body is run from a first glass surface to a second glass surface, each surface of which is sprayed with a TEFLON aerosol, and the force is measured to deform the span a distance of 5 mm. In the rig as described the force measured was approx. 1 gram.

Proximal section 122 of central portion 121 had its bending stiffness measured by the testing rig and procedure shown in FIG. 6C. As seen 40 mm length of proximal section 122 of central portion 121 of lead body is run from a first glass surface to a second glass surface, each surface of which is sprayed with a TEFLON aerosol, and the force is measured to deform the span a distance of 5 mm. In the rig as described the force measured was approx. 5 grams.

Distal section 1210 of central portion 121 had its bending stiffness measured by the testing rig and procedure shown in FIG. 6D. As seen a 40 mm linear length of distal section 1210 of central portion 121 of lead body is run from a first glass surface to a second glass surface, each surface of which is sprayed with a TEFLON aerosol, and the force is measured to deform the span until the distance above the glass surface is 10 mm. In the rig as described the force measured was approx. 15 grams.

Proximal section 125 of distal portion 123 had its bending stiffness measured by the testing rig and procedure shown in FIG. 6E. As seen a 40 mm length of proximal section 125 of distal portion 123 of lead body is run from a first glass surface to a second glass surface, each surface of which is sprayed with a TEFLON aerosol, and the force is measured to deform the span a distance of 5 mm. In the rig as described the force measured was approx. 2 grams.

Distal section 124 of distal portion 123 had its bending stiffness measured by the testing rig and procedure shown in FIG. 6F. As seen a 40 mm length of distal section 124 of distal portion 123 of lead body is run from a first glass surface to a second glass surface, each surface of which is sprayed with a TEFLON aerosol, and the force is measured to deform the span a distance of 5 mm. In the rig as described the force measured was approx. 10 grams.

Distal tip electrode 128 had its bending stiffness measured by the testing rig and procedure shown in FIG. 6G. As seen a 40 mm length of lead, starting from distal tip electrode 128 into the distal section 124 of distal portion 123 is run from a first glass surface to a second glass surface, each surface of which is sprayed with a TEFLON aerosol, and the force is measured to deform the span a distance of 5 mm. In the rig as described the force measured was approx. 20 grams.

Figure 7:
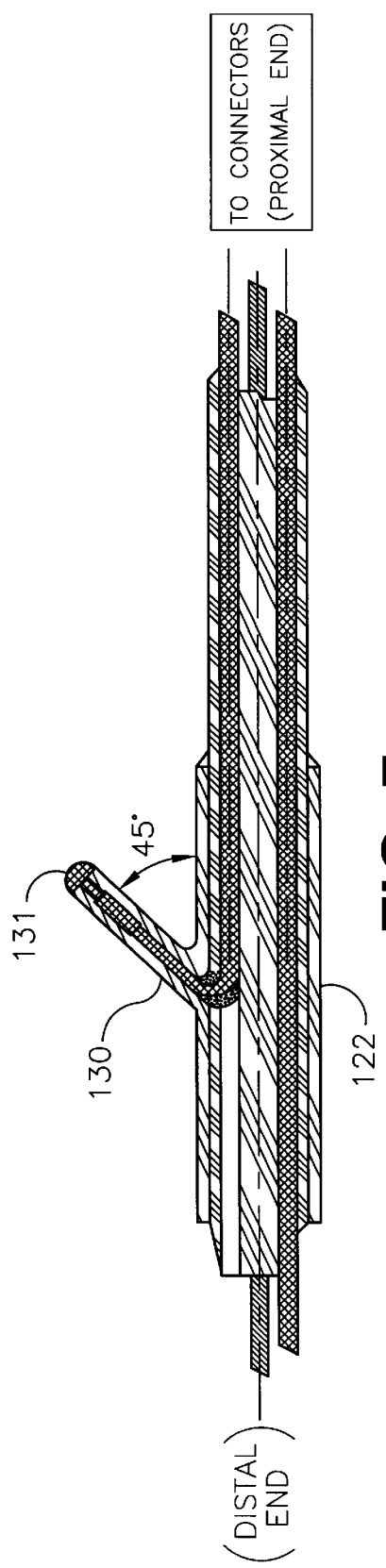
FIG. 7 depicts a detailed view of the construction of proximal section 122 and, in particular, of tine 130.

FIG. 7 depicts a detailed view of the construction of proximal section 122 and, in particular, of tine 130. As seen, a conductor is run from the connectors directly to tip electrode 131. As further seen, tine is disposed at an approximately 45° angle relative to lead body, and angled in the backward direction towards proximal end.

Figure 8:
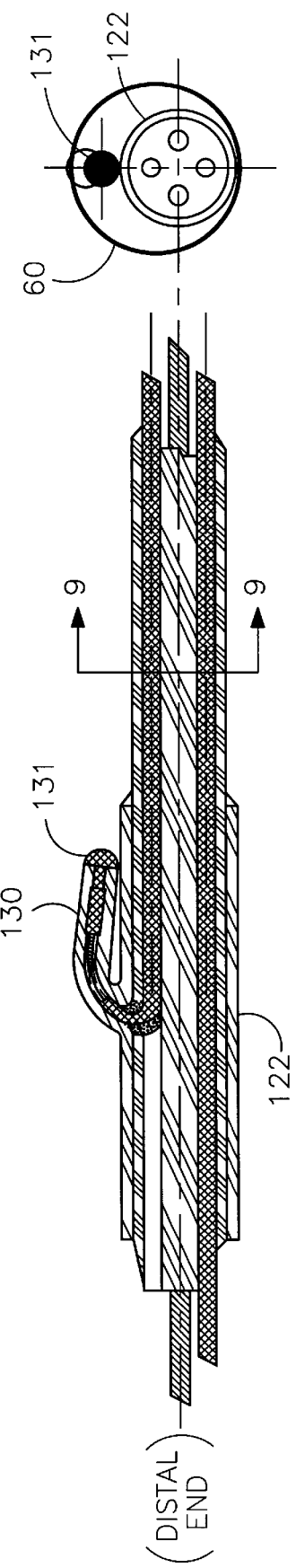
FIG. 8 depicts the tine folded back so as to fit within the introducer.

FIG. 8 depicts the tine folded back so as to fit within the introducer. As can be appreciated, the bending backwards of this tine and, in particular, the almost 180° bend the conductor makes may cause stresses to develop.

Figure 9:
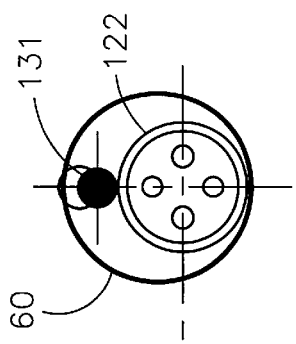
FIG. 9 is a sectional view taken across line 9—9 of FIG. 8 and depicts the lead having the tine folded back and fitted within an introducer sheath.

FIG. 9 is a sectional view taken across line 9—9 of FIG. 8 and depicts the lead having the tine folded back and fitted within an introducer sheath.

FIG. 10 depicts an alternative embodiment of lead and, in particular, a detailed view of a lead having an improved tine. In this embodiment, tine is the same as that shown in FIG. 7 but for its orientation, namely, in this embodiment, tine is angled forward towards distal end. In this embodiment, proximal section 122 further features a cavity 999 into which the tine may be folded to permit the lead to be introduced using a similar size introducer.

FIG. 11 depicts the tine folded forward for introduction and particularly shows the tine nestling into cavity 999.

FIG. 12 is a section view depicting the folded tine within an introducer sheath. As can be appreciated, this embodiment permits a smaller introducer sheath to be used, while also decreasing the likelihood of stress related problems which may develop in the tine or conductors to the tine.

Figure 13:
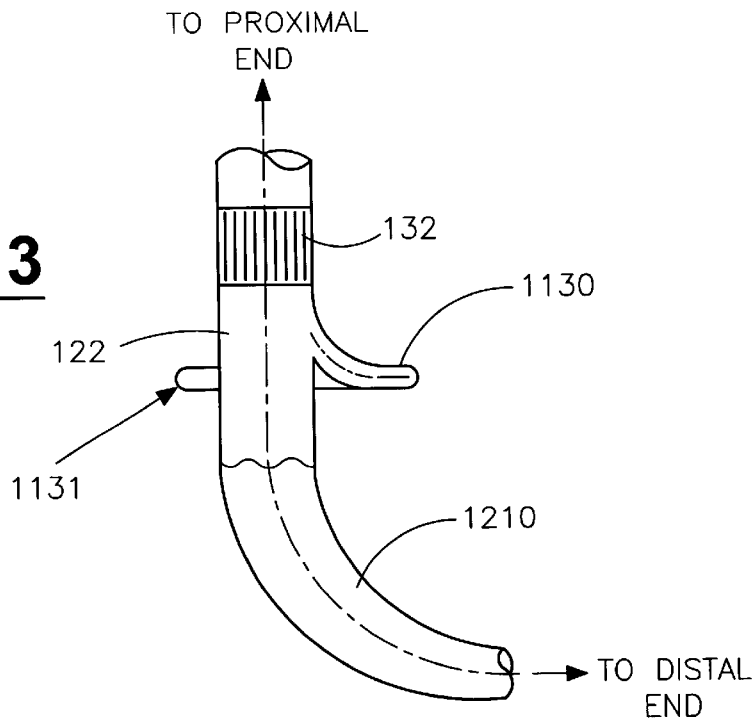
FIG. 13 depicts a still further embodiment of the present invention.

FIG. 13 depicts a still further embodiment of the present invention. In this embodiment, the proximal section 122 features an elongated angled and covered tine 1130. As seen, angled and covered tine 1130 is disposed so as to partially encompass a radial area of proximal section 122. As further seen, tine 1130 features a tip electrode 1131.

Figure 14:
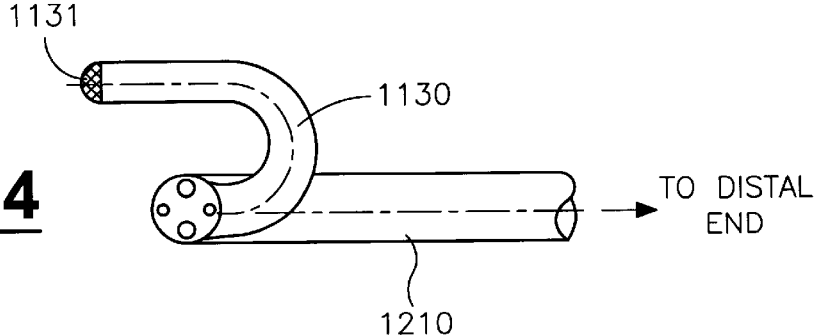
FIG. 14 is a sectional view taken along lead body further showing the tine 1130.

FIG. 14 is a sectional view taken along lead body further showing the tine 1130. All other elements of the lead in this embodiment are the same as those already described above.

Figure 15:
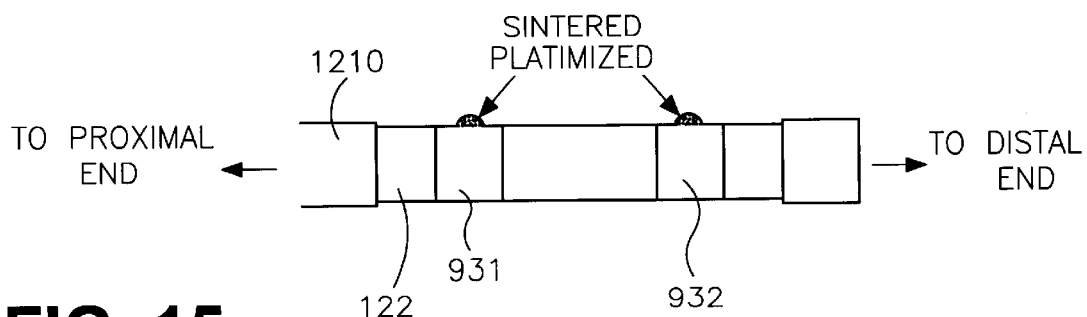
FIG. 15 shows a still further embodiment of the present invention.

FIG. 15 shows still further embodiments of the present invention. In this embodiment, the proximal section 122 features a pair of ring electrodes. First ring electrode 931 and second electrode 932 each feature bumps to provide a further ability to electrically couple with atrial tissue. The bumps comprise upraised sections along the electrode. These upraisings may be either generally hemispherical, elongated, cylindrical, shark fin-like, or any other symmetrical or non-symmetrical geometry to further provide a physical method for the metallic electrode to contact and thereby couple with the atrial tissue.

It is thus seen that there is provided a lead assembly which can be easily placed through an introducer, allowing longitudinal or axial movement of the lead with respect to the introducer without transverse kinking of the atrial tine or atrial tines on the lead. The invention further embodies the method of assembly of the tubing split element on the atrial tine lead, whereby it is in position to be quickly and efficiently introduced through the introducer by the physician. This provides the physician with a secure lead assembly enabling plural passes within the introducer, thereby providing for optimum positioning of the lead within the patient's heart, without incurring detrimental kinking to the atrial electrode or electrodes. Finally the invention includes a uniquely shaped and fashioned lead which provides excellent atrial electrode wall contact.

What is claimed is:

1. In combination with a lead introducer having an inner diameter, a lead assembly adapted for introduction into a patient's heart, the lead assembly comprising:
   a lead having a distal end and a proximal end, a longitudinal body extending from the proximal end to the distal end, at least one electrode being disposed at the distal end, a conductor being disposed within the body and electrically connecting the distal end electrode and the proximal end, and an atrial tine element positioned on said lead so as to be located within the patient's atrium when the distal end is positioned in the patient's ventricle, the atrial tine having an electrode and a conductor which electrically connects the atrial tine electrode to the lead proximal end; and
   a tubing split element positioned concentrically around said lead body, the element having a distal end which disposed distally from the atrial tine and a length extending proximally from the atrial tine, the element having a longitudinal split within which the atrial tine is positioned;
   wherein said lead has an outer body diameter which is less than said introducer inner diameter, and said tubing split element has an outer diameter just less than said introducer inner diameter, such that when said lead assembly is disposed within said introducer said tubing split element substantially fills a radial gap between said lead body and said introducer.

2. The combination as described in claim 1, wherein said tubing split element comprises TEFLON™ type material.

3. The lead assembly described in claim 1, wherein said lead has a plurality of atrial tines, and said element comprises a plurality of longitudinal splits positioned for receiving respective ones of said atrial tines.

4. A lead assembly adapted for use with an introducer, the introducer having a predetermined inner diameter for receiving said assembly so as to guide said lead assembly into a patient's heart, comprising:
   a lead for delivering pulse energy to the patient's heart, having a tubular lead body extending substantially the length of said lead, said body having an outer diameter less than said introducer inner diameter, and at least one atrial tine extending from said body, said atrial tine having an electrode thereon, and a conductor connecting said electrode electrically to the proximal end of said lead; and
   a tubing split element assembled on said lead, said element being substantially tubular and having an inner diameter substantially matching said lead body outer diameter and positioned concentrically around said body so as to extend distally and proximally from said at least one atrial electrode, said element having an outer diameter that substantially matches said introducer inner diameter so that said lead and said element together can be moved longitudinally within said introducer element, said element having split means for receiving said at least one atrial electrode and restraining it from transverse movement, whereby when said lead is moved longitudinally within said introducer said at least one atrial tine is not stressed transversely.

5. The assembly as described in claim 4, wherein said element has a length in the range of about 8–15 cm.

6. The assembly as described in claim 5, wherein said split means comprises a longitudinal split in said element for receiving said at least one atrial tine.

7. The assembly as described in claim 6, wherein said split extends the length of said element.

8. The assembly as described in claim 6, wherein said lead comprises at least two atrial tines, and said split means comprises at least two longitudinal splits positioned to receive said at least two atrial tines.

9. The assembly as described in claim 4, wherein said element is a single piece of TEFLON™ type material.

10. A method of making a lead assembly which is adapted for introduction through an introducer, said introducer having a predetermined inner diameter for receiving said assembly, comprising:
   making a lead having a body extending from a proximal end to a distal end, said body having an outer diameter less than said introducer inner diameter and carrying therein conductor means for electrically connecting to at least one electrode, said making including forming at least one atrial tine on said lead, said atrial tine having a radial extension from said body and having an electrode and a conductor for connecting said electrode to said conductor means, and
   placing around said lead body in the area of said at least one atrial tine a tubing split element having a radial thickness substantially equal to the difference between said lead body outer diameter and said introducer inner diameter, and having a longitudinal split for receiving said at least one atrial tine and constraining it from transverse movement when said lead assembly is moved longitudinally within said introducer.

11. A medical electrical lead and introducer system comprising:

an introducer assembly, the introducer assembly having an introducer sheath, the introducer sheath having means for permitting the sheath to be removed from around a lead disposed therethrough without having to be removed over a end of said lead;

a single pass lead disposed through the introducer assembly, the single pass lead having a first electrode disposed to electrically contact atrial tissue and a second electrode disposed to electrically contact ventricular tissue; the single pass lead having a lead body, the lead body having a bent pre-form portion; and a removable tubing element disposed around the lead body and within the sheath.

12. The medical electrical lead and introducer system according to claim 11 wherein the sheath has a first radius, a portion of the lead body disposed within the sheath has a second radius, the first radius larger than the second radius, the removable tubing element has a thickness substantially equal to the difference between the first radius and second radius.

13. The medical electrical lead and introducer system according to claim 12 wherein the removable tubing element has an elongated slit, the first electrode being configured to electrically contact atrial tissue, the first electrode being mounted on a tine extending away from the lead body, the tine being positioned within the slit when the lead is disposed through the introducer.

14. The medical electrical lead and introducer system according to claim 11 wherein the lead body has differing stiffnesses along different portions.

15. A medical electrical lead comprising a connector assembly adopted to be coupled to an implantable pulse generator; and a lead body coupled to the connector assembly, the lead body having a first section, a second section coupled to the first section and a third section coupled to the second section, the first section having a first stiffness, the second section having a second stiffness and the third section having a third stiffness, the second stiffness greater than the first stiffness and the third stiffness, the third stiffness greater by a factor of ten than the first stiffness, the second section having a bend.

16. The medical electrical lead of claim 15 wherein the second stiffness is greater by a factor of fifteen than the first stiffness.

17. The medical electrical lead of claim 15 wherein the bend of the second section is between 45 and 135 degrees.

18. The medical electrical lead of claim 17 wherein the bend of the second section ninety degrees.

19. The medical electrical lead of claim 15 wherein the second section has a first electrode.

20. The medical electrical lead of claim 19 wherein the second section has a second electrode.

21. The medical electrical lead of claim 20 wherein the second section has a tine, the second electrode being disposed on the tine.

22. The medical electrical lead of claim 21 wherein the tine extends away from lead body.

23. The medical electrical lead of claim 22 wherein the tine extends downwards away from lead body.

24. The medical electrical lead of claim 15 wherein the third section is straight.

25. The medical electrical lead of claim 24 wherein the third section has a defibrillation electrode.

26. The medical electrical lead of claim 15 further comprising a fourth section along the lead body, the fourth section positioned between second and third sections.

27. The medical electrical lead of claim 26 wherein the fourth section has a fourth stiffness, the fourth stiffness greater that the first stiffness but less than the third stiffness.

28. The medical electrical lead of claim 27 wherein the fourth stiffness is less than one-half the stiffness of the third section.

29. A medical electrical lead and introducer system comprising:

an introducer, the introducer having a sheath and a tubing split element disposed within the sheath, the tubing split element having a first slot;

a lead disposed within the tubing split element, the lead having a tine, the tine having an electrode, the tine positioned within the first slot of the tubing split element.

30. The medical electrical lead and introducer system according to claim 29 wherein the lead has a lead body, the lead body having a first section, a second section coupled to the first section and a third section coupled to the second section, the first section having a first stiffness, the second section having a second stiffness and the third section having a third stiffness, the second stiffness greater than the first stiffness and the third stiffness, the third stiffness greater by a factor of ten than the first stiffness, the second section having a bend.

31. The medical electrical lead of claim 30 wherein the second stiffness is greater by a factor of fifteen than the first stiffness.

32. The medical electrical lead of claim 30 wherein the bend of the second section is between 45 and 135 degrees.

33. The medical electrical lead of claim 32 wherein the bend of the second section ninety degrees.

34. The medical electrical lead of claim 30 wherein the second section has a first electrode.

35. The medical electrical lead of claim 34 wherein the second section has a second electrode.

36. The medical electrical lead of claim 35 wherein the second section has a tine, the second electrode disposed on the tine.

37. The medical electrical lead of claim 36 wherein the tine extends away from lead body.

38. The medical electrical lead of claim 37 wherein the tine extends downwards away from lead body.

39. The medical electrical lead of claim 30 wherein the third section is straight.

40. The medical electrical lead of claim 39 wherein the third section has a defibrillation electrode.

41. The medical electrical lead of claim 30 wherein the lead has a fourth section, the fourth section positioned between second and third sections.

42. The medical electrical lead of claim 41 wherein the fourth section has a fourth stiffness, the fourth stiffness greater that the first stiffness but less than the third stiffness.

43. The medical electrical lead of claim 42 wherein the fourth stiffness is less than one-half the stiffness of the third section.

* * * * *